(12) United States Patent
Hudson et al.

(10) Patent No.: US 9,603,563 B2
(45) Date of Patent: Mar. 28, 2017

(54) SKIN PENETRATION DEVICE

(75) Inventors: Christopher Hudson, Oxfordshire (GB); Timothy Muller, Witney (GB)

(73) Assignee: OWEN MUMFORD LIMITED, Oxford (GB)

( * ) Notice: Subject to any disclaimer, the term of this patent is extended or adjusted under 35 U.S.C. 154(b) by 127 days.

(21) Appl. No.: 14/110,526

(22) PCT Filed: Apr. 4, 2012

(86) PCT No.: PCT/GB2012/050761
§ 371 (c)(1),
(2), (4) Date: Jan. 9, 2014

(87) PCT Pub. No.: WO2012/137001
PCT Pub. Date: Oct. 11, 2012

(65) Prior Publication Data
US 2014/0121691 A1    May 1, 2014

Related U.S. Application Data

(60) Provisional application No. 61/473,251, filed on Apr. 8, 2011.

(30) Foreign Application Priority Data

Apr. 8, 2011 (GB) .................................. 1105950.8

(51) Int. Cl.
*A61B 17/14*   (2006.01)
*A61B 17/32*   (2006.01)
(Continued)

(52) U.S. Cl.
CPC ...... *A61B 5/1519* (2013.01); *A61B 5/150022* (2013.01); *A61B 5/15113* (2013.01);
(Continued)

(58) Field of Classification Search
CPC ....... A61B 5/14; A61B 5/1405; A61B 5/1411; A61B 5/15; A61B 5/15007;
(Continued)

(56) References Cited

U.S. PATENT DOCUMENTS 5,282,822 A    2/1994  Macors et al.
5,464,418 A   11/1995  Schraga
(Continued)

FOREIGN PATENT DOCUMENTS

EP    0 414 563 A1    2/1991
EP    0 776 633 A1    6/1997
(Continued)

OTHER PUBLICATIONS

International Search Report dated Sep. 19, 2012, corresponding to PCT/GB2012/050761.
(Continued)

*Primary Examiner* — Melanie Tyson
(74) *Attorney, Agent, or Firm* — Young & Thompson

(57) ABSTRACT

A lancing device includes a housing (10, 12) and a lancet holder movably mounted within the housing. The lancet holder has a forward portion defining a socket (30) for partially surrounding and retaining in use the rear portion of a lancet. A lancet release element (40, 42) can be moved forward to cooperate with lugs on the socket to expand it to allow insertion and/or removal of the lancet with minimal insertion or withdrawal force.

10 Claims, 9 Drawing Sheets

(51) Int. Cl.
 *A61B 5/151* (2006.01)
 *A61B 5/15* (2006.01)
(52) U.S. Cl.
 CPC .... *A61B 5/150114* (2013.01); *A61B 5/15117* (2013.01); *A61B 5/150183* (2013.01); *A61B 5/15194* (2013.01); *A61B 5/150412* (2013.01); *A61B 5/150503* (2013.01); *A61B 5/150595* (2013.01); *A61B 5/150809* (2013.01); *A61B 5/150824* (2013.01)
(58) Field of Classification Search
 CPC ........ A61B 5/150167; A61B 5/150175; A61B 5/150183; A61B 5/15019; A61B 5/150198; A61B 5/151; A61B 5/15101; A61B 5/15103; A61B 5/15107; A61B 5/15109; A61B 5/15111; A61B 5/15113; A61B 5/15115; A61B 5/15117; A61B 5/15186; A61B 5/15188; A61B 5/1519; A61B 5/15192; A61B 5/15194; A61B 5/15196; A61B 5/15198
 See application file for complete search history.

(56) References Cited

U.S. PATENT DOCUMENTS

| | | | |
|---|---|---|---|
| 5,613,978 A * | 3/1997 | Harding | A61B 5/1411 606/181 |
| 5,916,230 A * | 6/1999 | Brenneman | A61B 5/1411 606/172 |
| 6,022,366 A | 2/2000 | Schraga | |
| 6,197,040 B1 * | 3/2001 | LeVaughn | A61B 5/1411 600/583 |
| 6,346,114 B1 | 2/2002 | Schraga | |
| 6,852,119 B1 | 2/2005 | Abulhaj et al. | |
| 6,875,223 B2 | 4/2005 | Argauer | |
| 6,929,650 B2 | 8/2005 | Fukuzawa et al. | |
| 7,670,352 B1 | 3/2010 | Starnes | |
| 8,123,771 B2 | 2/2012 | Matsumoto | |
| 8,187,295 B2 | 5/2012 | Uehata et al. | |
| 8,308,747 B2 | 11/2012 | Fukuzawa | |
| 8,419,761 B2 | 4/2013 | Hong | |
| 8,636,758 B2 | 1/2014 | Fritz et al. | |
| 2001/0027326 A1 | 10/2001 | Schraga | |
| 2002/0082633 A1 | 6/2002 | Schraga | |
| 2003/0050656 A1 | 3/2003 | Schraga | |
| 2003/0100913 A1 | 5/2003 | Shi | |
| 2004/0098010 A1 * | 5/2004 | Davison et al. | 606/181 |
| 2004/0186500 A1 | 9/2004 | Koike et al. | |
| 2004/0225311 A1 | 11/2004 | Levaughn et al. | |
| 2005/0245955 A1 | 11/2005 | Schraga | |
| 2006/0241669 A1 | 10/2006 | Stout et al. | |
| 2006/0247670 A1 | 11/2006 | LeVaughn et al. | |
| 2007/0055298 A1 * | 3/2007 | Uehata et al. | 606/181 |
| 2009/0036916 A1 | 2/2009 | Fukuzawa et al. | |
| 2009/0043326 A1 | 2/2009 | Zhong et al. | |
| 2009/0093832 A1 | 4/2009 | Fukuzawa | |
| 2009/0163944 A1 | 6/2009 | Nagao et al. | |
| 2010/0094324 A1 | 4/2010 | Huang et al. | |
| 2010/0121366 A1 | 5/2010 | Weiss et al. | |
| 2010/0324582 A1 * | 12/2010 | Nicholls | A61B 5/1411 606/182 |
| 2011/0276074 A1 | 11/2011 | Shi | |

FOREIGN PATENT DOCUMENTS

| | | |
|---|---|---|
| EP | 0 885 590 A1 | 12/1998 |
| EP | 1 074 219 | 2/2001 |
| EP | 1 074 219 A2 | 2/2001 |
| EP | 1 290 977 A2 | 3/2003 |
| EP | 1 464 283 A1 | 10/2004 |
| EP | 2 050 393 A1 | 4/2009 |
| EP | 2 174 591 A1 | 4/2010 |
| GB | 2451840 | 2/2009 |
| WO | 93/09723 A1 | 5/1993 |
| WO | 97/46157 A1 | 12/1997 |
| WO | 98/06331 | 2/1998 |
| WO | 99/63897 A1 | 12/1999 |
| WO | 01/28423 | 4/2001 |
| WO | 02/36010 A1 | 5/2002 |
| WO | 02/054952 A1 | 7/2002 |
| WO | 02/065910 A1 | 8/2002 |
| WO | 03/005906 A1 | 1/2003 |
| WO | 03/022130 A2 | 3/2003 |
| WO | 2004/010871 A1 | 2/2004 |
| WO | 2004/091402 A1 | 10/2004 |
| WO | 2004/103177 A1 | 12/2004 |
| WO | 2005/018422 A2 | 3/2005 |
| WO | 2005/034753 A1 | 4/2005 |
| WO | 2005/070283 A1 | 8/2005 |
| WO | 2005/070293 A2 | 8/2005 |
| WO | 2005/089333 A2 | 9/2005 |
| WO | 2006/004664 A1 | 1/2006 |
| WO | 2006/067120 A1 | 6/2006 |
| WO | 2006/096539 | 9/2006 |
| WO | 2007/102576 A1 | 9/2007 |
| WO | 2007/105617 A1 | 9/2007 |
| WO | 2007/129757 A1 | 11/2007 |
| WO | 2007/130830 A2 | 11/2007 |
| WO | 2007/146913 A2 | 12/2007 |
| WO | 2008/041438 A1 | 4/2008 |
| WO | 2008/045960 A2 | 4/2008 |
| WO | 2008/098046 A1 | 8/2008 |
| WO | 2008/111936 A1 | 9/2008 |
| WO | 2008/121680 A2 | 10/2008 |
| WO | 2008/157610 A1 | 12/2008 |
| WO | 2009/022131 | 2/2009 |
| WO | 2009/022136 | 2/2009 |
| WO | 2009/022144 | 2/2009 |
| WO | 2009/035084 A1 | 3/2009 |
| WO | 2009/069720 A1 | 6/2009 |
| WO | 2009/136164 A2 | 11/2009 |
| WO | 2009/136171 | 11/2009 |
| WO | 2009/136172 A2 | 11/2009 |
| WO | 2009/148431 A1 | 12/2009 |
| WO | 2010/019734 A1 | 2/2010 |
| WO | 2010/025072 A1 | 3/2010 |
| WO | 2010/064998 A1 | 6/2010 |
| WO | 2010/080585 A1 | 7/2010 |
| WO | 2010/081265 A1 | 7/2010 |

OTHER PUBLICATIONS

British Search Report dated Aug. 4, 2011, corresponding to the Foreign Priority Application No. GB1105950.8.

* cited by examiner

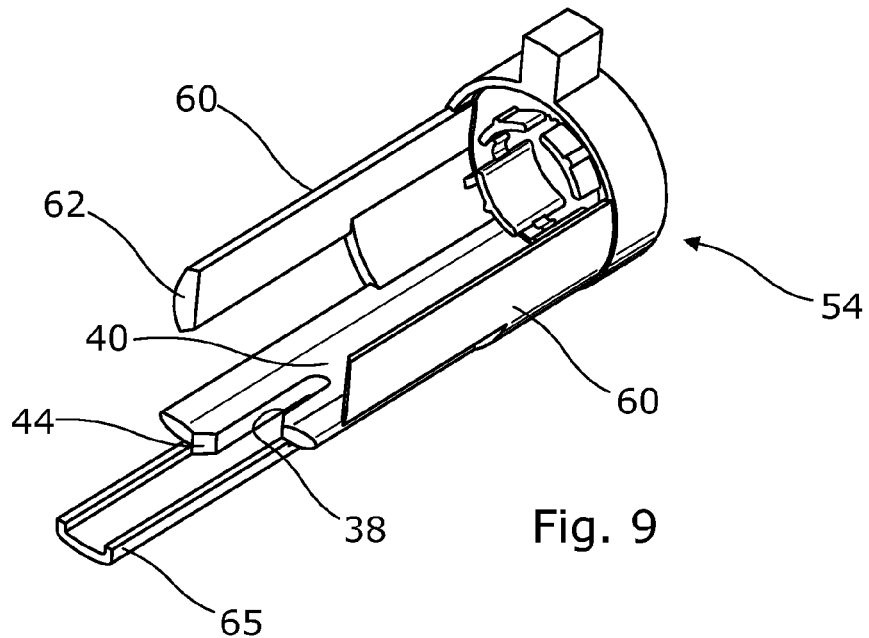
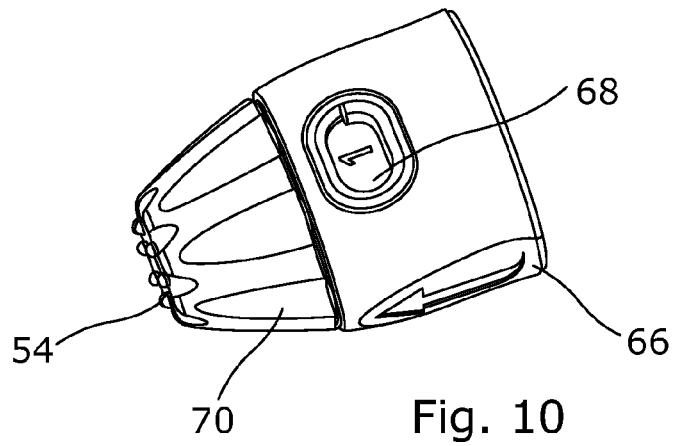
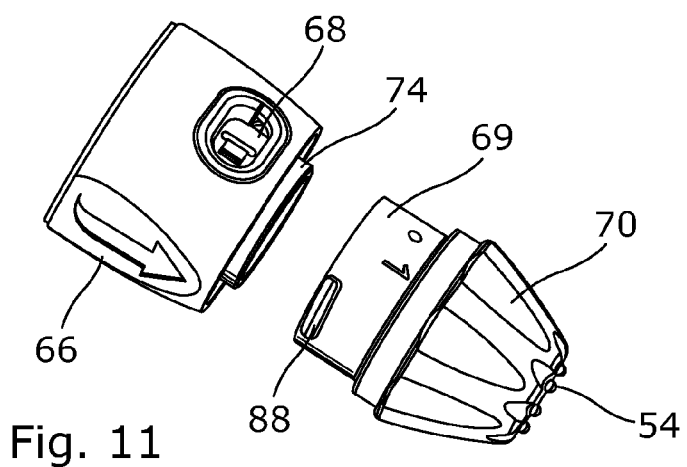

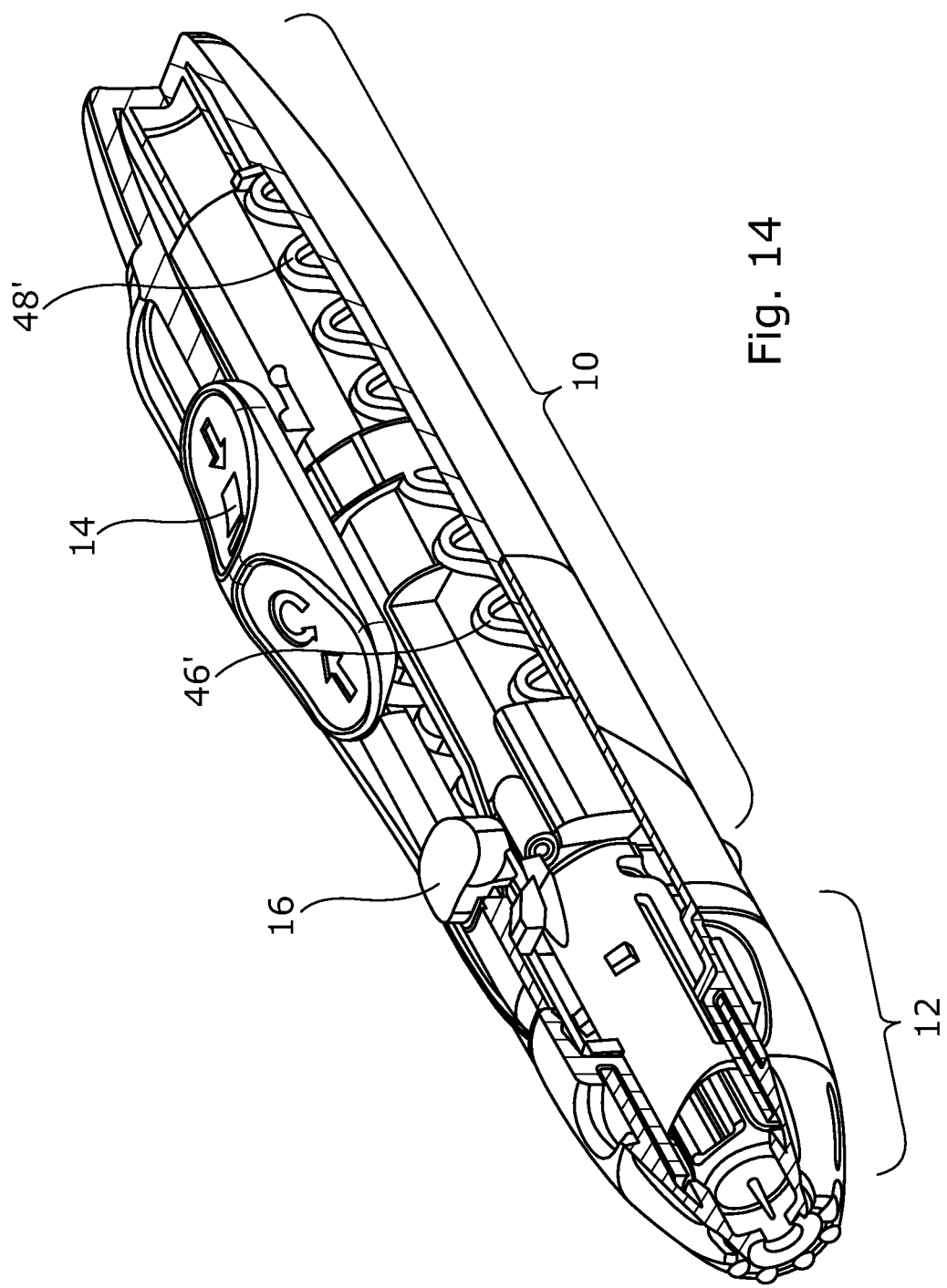

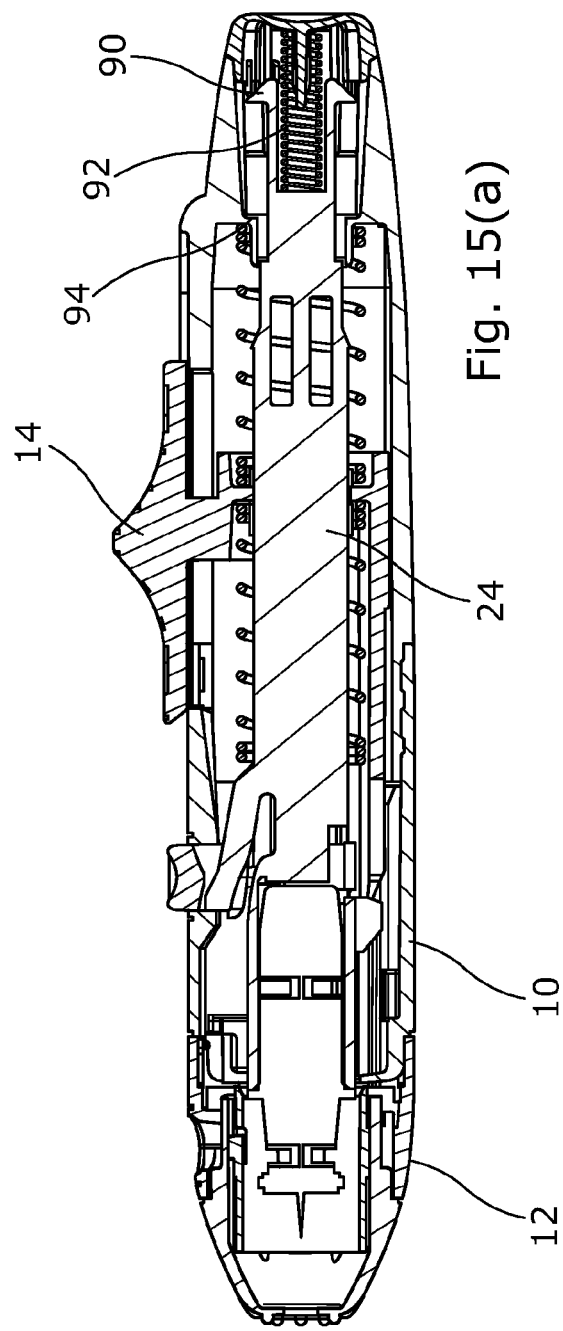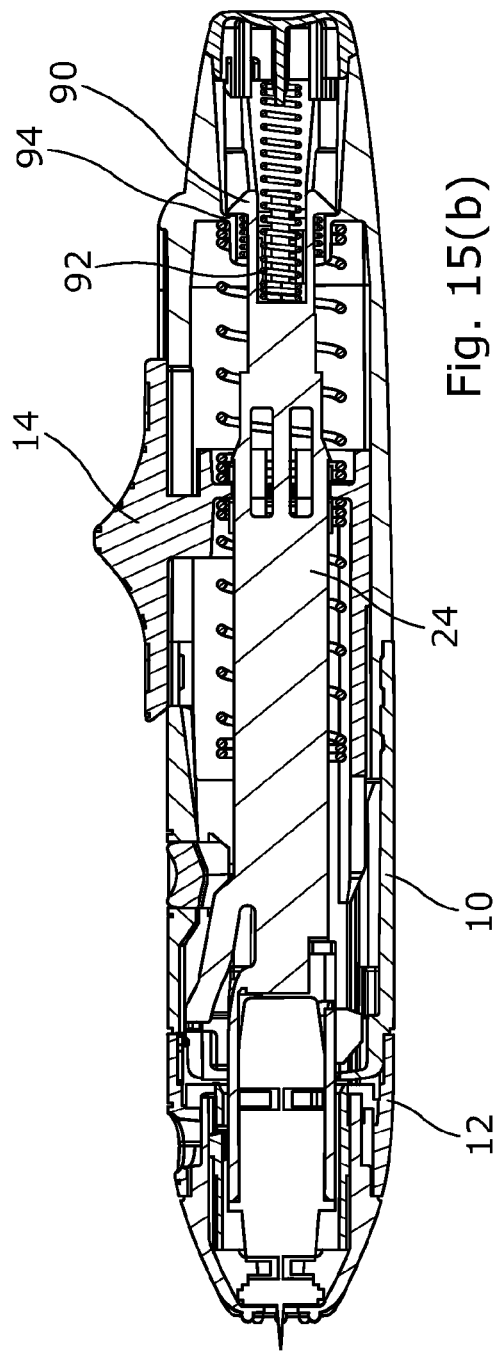

SKIN PENETRATION DEVICE

This invention relates to skin penetration devices and in particular, but not exclusively, to lancing devices. As will be evident, certain features disclosed herein may be used in applications other than lancing devices, for example in injection devices.

There are many instances where it is required to prick the skin to obtain a sample of capillary blood for e.g. testing for blood glucose level in diabetics. It is important that such devices operate efficiently and can be readily assembled during manufacture. There is a considerable benefit in reducing the number of component parts and thereby facilitating manufacture and assembly thereof. At the same time, it is important to provide safe and reliable operation for the end user.

In one aspect, many lancing devices are designed to be used with a disposable lancet, with the lancet device itself being reused many times. Prior to a lancing operation, a fresh lancet is typically loaded into a lancet holder in the device which is then cocked and fired. After use, the spent lancet, now contaminated with blood, must be removed for disposal. The connection between the lancet holder and lancet needs to be sufficient to retain the lancet securely during operation. It is common for this to be a push fit with a mild form of detent action. In order to release such a lancet it is common to provide a push rod arrangement, which pushes the lancet clear of the holder to eject it. There is a risk with this operation that actively pushing the spent lancet clear of the holder could cause an inadvertent needle stick injury. Also, there is a risk that the pressure on the lancet, once free of the holder, will cause it to catapult or fire forward. We have therefore designed an arrangement in which the lancet holder can securely retain or grip the lancet but which can be released to allow the spent lancet to drop out without requiring pushing of the lancet.

Another aspect of those lancing devices where the lancet is a push fit into the lancet holder and held there by friction or a detent action, is that there is a significant insertion force required to load the lancet. This can be problematic because it may result in the user inadvertently dislodging the safety cap that typically covers the lancet tip before use thereby exposing or bending the tip, both of which are to be avoided. By providing an arrangement in which a socket in the lancet holder can be expanded means that a lancet can be loaded into the lancet holder with practically zero insertion force, yet be securely retained once loaded.

In our earlier Autolet® Life Clinisafe device a wedge element is mounted to be driven transversely to force adjacent wall edges of a lancet holder apart. This transverse wedging action places significant constraints on the design of the device. US2006/0247670, US2009/0043326 and WO2006/096539 disclose arrangements in which a lancet holder is caused to expand by driving a protuberance or wedge transversely into a slot of a slotted lancet holder sleeve.

Accordingly, in one aspect, this invention provides a lancing device having:
a housing;
a lancet holder movably mounted within said housing for movement in a lancing direction, the lancet holder having a forward portion defining a socket for partially surrounding and retaining in use a rear portion of a lancet, the socket being expandable to allow insertion and/or removal of said lancet, and a lancet release element movable in a direction generally parallel to said lancing direction between a rest and a release position to cause said socket to move between a lancet retaining condition and an expanded condition.

Moving the release element in a direction generally parallel to the lancing direction may allow a longer stroke of movement and therefore less force, than those in which a wedge is inserted transversely.

Conveniently said socket is defined by a generally cylindrical wall of resilient material having a slot therein to allow resilient expansion and/or contraction. The cylindrical wall may be provided with radially outwardly extending abutments spaced one to either side of said slot, with said release element having respective cam surfaces cooperating with said abutment whereby movement of the release element in a direction generally parallel to the lancing direction causes movement of the socket between its lancet retaining condition and its expanded condition. Disposing the lancet release element for longitudinal movement means that the release action of the release element does not project or encroach into the interior of the socket. This means that there is greater design flexibility in designing the release action in terms of axial extent of movement of the release element, and the proportion of the stroke of movement over which expansion of the socket is effected, and the mechanical advantage and/or activation pressure required.

Conveniently, the wall of the socket is shaped, and the abutments are angularly disposed to provide an 'overlap' so that, to expand the socket the abutments are squeezed towards each other to expand the socket, although arrangements in which the abutments are squeezed apart to expand the socket are possible. Preferably the wall of the socket has a slot comprising forward and rearward angularly offset generally longitudinal extending portions, to provide a wrapping or overlap effect. The overlap may ensure that the lancet in use is held more securely against lateral movement during loading and unloading. Conveniently, said lancet release element is additionally movable to cock the lancet holder. Not only is this technically advantageous as it may allow a reduction in component design and a simpler mechanism, but it also provides intuitive operation.

In devices such as those described above and indeed in devices in which the lancet is pushed out actively, we have found that a possible difficulty arises if the lancet holder moves forward during the release operation. Accordingly, we have designed an arrangement which, when a lancet release element is moved to eject a lancet, the movement thereof is effective also to hold or limit forward movement.

Accordingly, in another aspect, this invention provides a lancing device having:
a housing;
a lancet holder movably mounted within said housing, the lancet holder having a forward portion for receiving in use a lancet, and
a lancet release element for being moved to allow release of a lancet from said lancet holder,
wherein movement of said lancet release element to release the lancet causes at least one of holding, or limiting, of forward movement of said lancet holder.

Conveniently said housing, or a component associated therewith, includes a lancet holder restraining element movable between a position in which it blocks forward movement of said lancet holder, and a free position in which forward movement of the lancet holder is not blocked thereby. Said lancet release element may include a control surface which, as said lancet release element is moved to release the lancet engages said locking element to move it to its blocking position.

Where the lancing device includes a trigger arrangement operable to latch and release said lancet holder for movement under the influence of a drive spring, said lancet holder restricting element is conveniently part of said trigger arrangement.

A common design of many lancing devices is to provide a housing which has a forward nose portion that is removable to allow loading and unloading of the lancet, with the nose portion providing a skin contact surface with a small aperture through which the tip of the lancet projects when fired. Where such devices also incorporate an active or passive lancet ejection action, it is important that the nose portion is removed before the lancet is ejected otherwise the user may inadvertently eject the lancet leaving it loose in the lancet housing with the risk that it moves again to project its tip through the housing, thereby leading to contamination; alternatively the unconstrained lancet may drop out of the housing the next time it is opened, before the user is ready to dispose of it. We have therefore designed an arrangement which ensures that the effective ejection action of the lancet is at least resisted until the nose portion has been removed.

Accordingly, in another aspect, this invention provides a lancing device having:

a housing comprising a main body portion and a forward nose portion removable and replaceable to allow loading and unloading of a lancet in use;

a lancet holder movably mounted in said housing and having a forward portion for receiving a lancet in use;

a lancet release element movable between a rest position and a release position, wherein movement of said lancet release element to its release position is resisted by said forward nose portion when connected to said main body portion.

In one embodiment, the presence of the forward nose portion effectively blocks movement of the lancet release element to its release position as it is not possible to force the nose portion off the device by pressure applied to the lancet release element. In another embodiment the device may be designed so that if an attempt is made to force the lancet release element to its release position with the nose portion still in place, the nose portion is ejected. Ejection of the nose portion may be an intended action prior to lancet ejection, or it may be flagged to the user as a misuse.

Conveniently said lancet release element is movable longitudinally and includes an elongate extension adapted to cooperate with said forward nose portion to prevent movement.

In skin penetration devices such as lancets and injection devices, it is often required to adjust the penetration depth of the penetration element in accordance with the skin thickness and the particular penetration operation. It is common to provide in, for example, lancing devices, a housing with a threaded nose portion that can be screwed in or out to adjust its axial position relative to a datum position such as the lancet holder stop position (or forwardmost position). The components of such devices are commonly injection-moulded and forming the helical thread forms on the cooperating surfaces of the components requires complex moulds. Furthermore, once moulded, assembly of the components requires screwing one on to the other which again requires angular registration and a more complex assembly operation. We have therefore designed an alternative arrangement which obviates the need for continuous thread forms on either component.

Accordingly, in another aspect, this invention provides a skin penetration device including:

a housing;

a movable insertion element disposed in said housing and having a sharp tip and adapted to be inserted into the skin of a recipient;

a depth penetration arrangement comprising a relatively fixed portion forming part of or secured to said housing, and a depth adjusting portion being mounted for angular movement about an axis on said relatively fixed portion;

one of the relatively fixed portion and the depth adjusting portion having a cam track defined by an interrupted cam surface, and the other having a cam follower adapted to cooperate with said cam track whereby relative rotation of said depth adjusting portion and said fixed portion varies the relative axial position thereof.

Conveniently said relatively fixed portion and said skin contacting portion include respective detent elements to provide a detent action at spaced angular positions. Advantageously, a stop surface is associated with said cam surface to limit relative rotation of said relatively movable member. Said interrupted cam surface may follow a generally helical path with respect to the axis, the cam surface including alternate opposite facing cam face elements together defining said cam track for said cam follower.

Preferably the cam surface elements are of lesser circumferential extent than said cam follower.

Conveniently at least one of the cam surface and said cam follower are resiliently deformable to allow said cam follower to be introduced into said cam track by the application of an axial load in a push fit operation. Although either option is possible the cam follower is conveniently provided on said depth adjusting portion with said cam track being provided on said relatively fixed portion.

It is desirable to ensure that once the lancing device has been locked, a loaded lancet is not removed until the device has been fired. We have therefore designed a device in which when the lancet is in a cocked condition, the lancet release mechanism is inhibited until after the device has been fired.

Accordingly, in another aspect, we provide a lancing device having:

a housing;

a lancet holder removably mounted within said housing, the lancet holder having a forward portion for receiving in use a lancet;

a lancet release element for being removed to allow release of a lancet from said lancet holder;

a trigger arrangement operable to latch and release said lancet holder for movement under the influence of a drive spring, said trigger arrangement including a trigger element which, during or after said lancet holder is latched, moves to an armed position ready to fire, and wherein when the lancet holder is latched, with the trigger arrangement in its armed position, the trigger arrangement blocks effective movement of said lancet release element.

Conveniently said trigger element projects from the surface of said housing when in the armed condition and the lancet release element comprises an externally accessible manually operable control element, and the trigger element in its armed position lies in the projected path of the control element.

In each of the above aspects forward movement of the lancet holder may be limited in various ways. In one preferred arrangement the lancet holder may have an abutment surface at or towards its rear end which moves into abutment with an abutment surface on the housing or a component relatively fixed thereto to define the forwardmost position of the lancet holder.

Whilst the invention has been described above, it extends to any inventive combination of the features set out above, or in the following description or drawings. It will be understood the features of the various aspects of this invention may be adopted in different aspects to provide innovative combinations.

The invention may be performed in various ways and, by way of example only, various embodiments of a lancing device in accordance with this invention and a modification thereof will now be described, reference being made to the accompanying drawings in which.

Figure 4A:
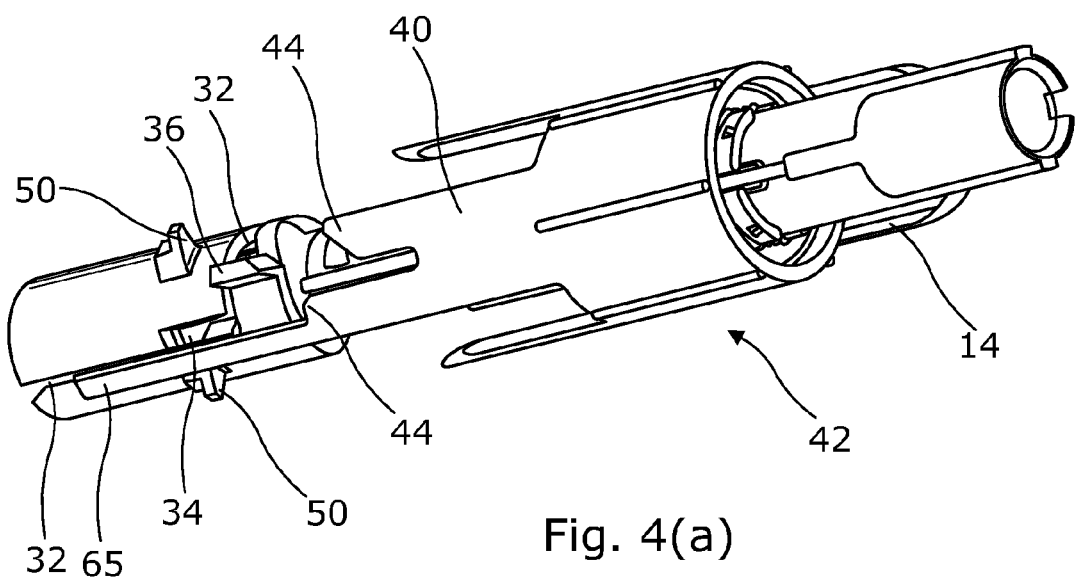
Figure 4B:
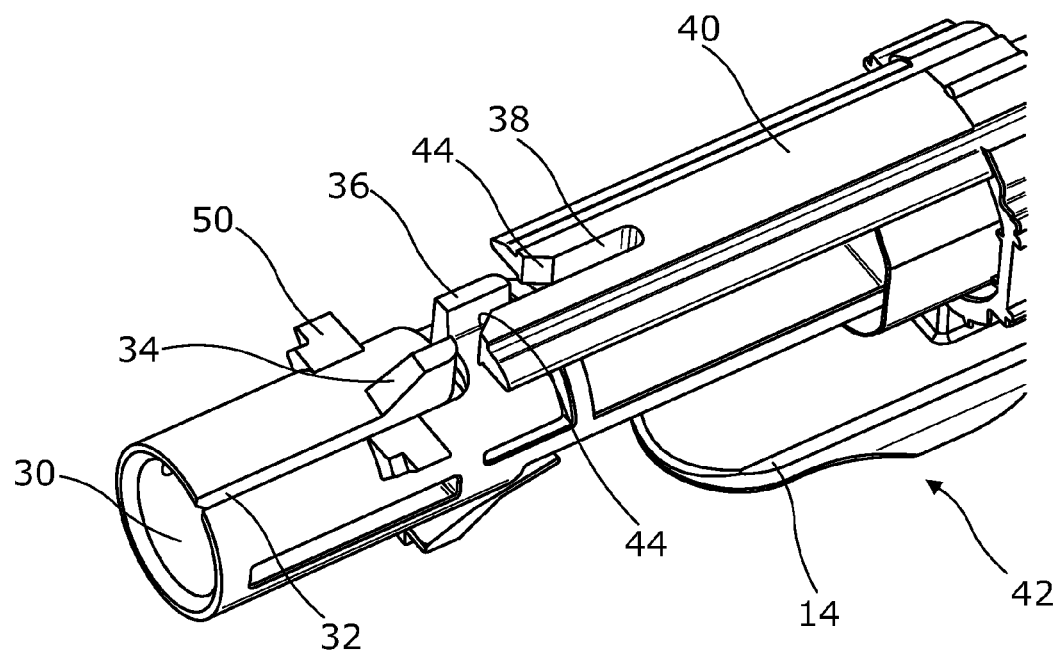
Figure 5:
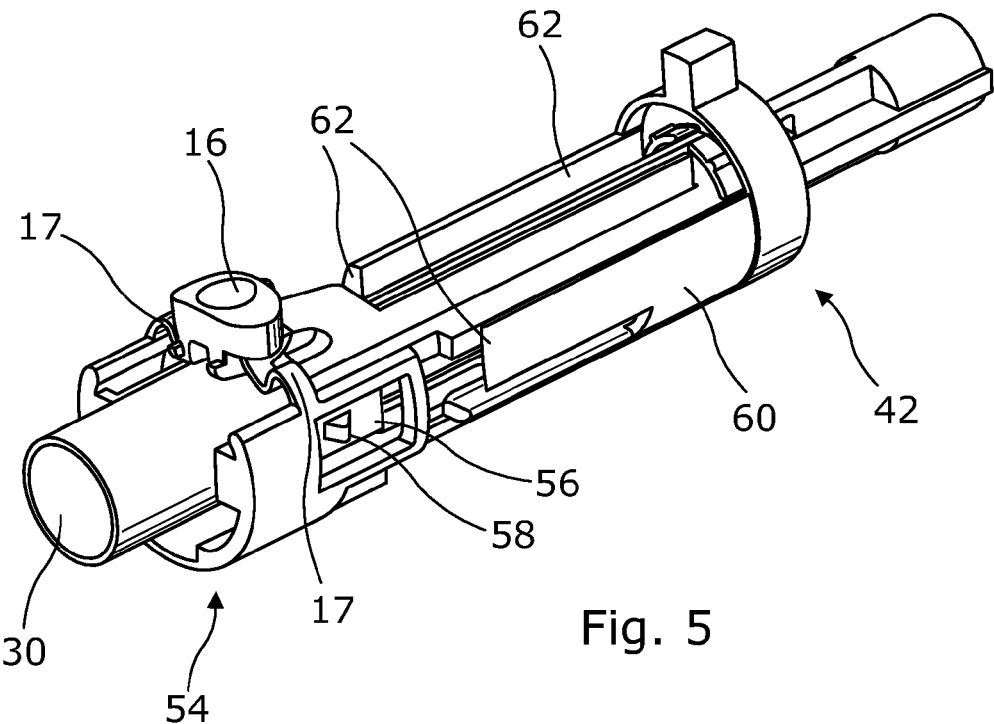
Figure 6:
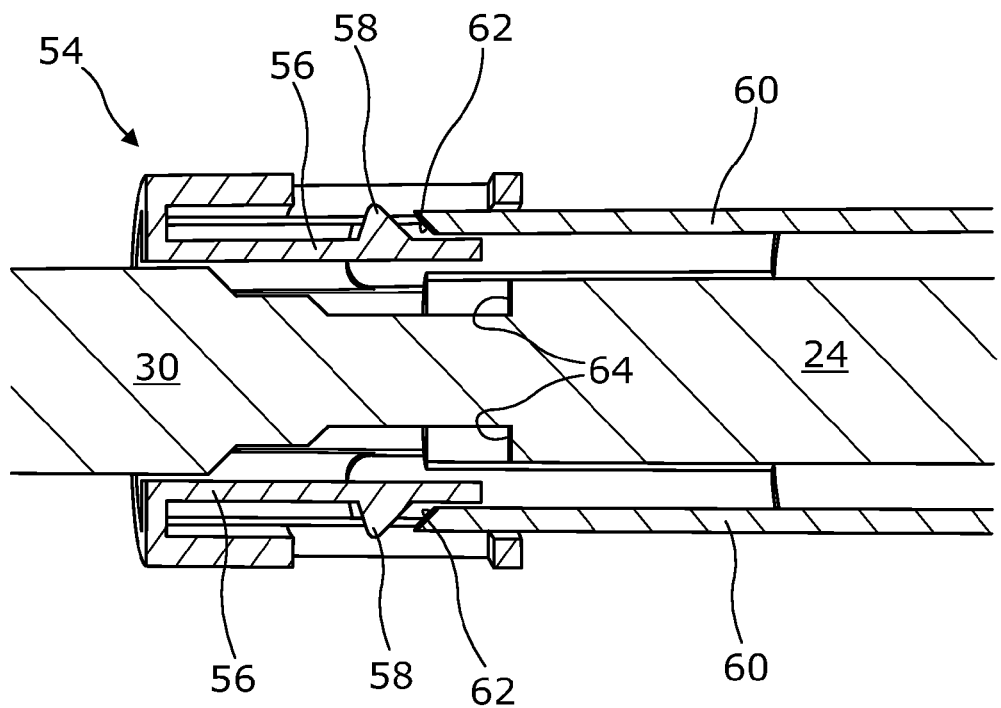
Figure 7:
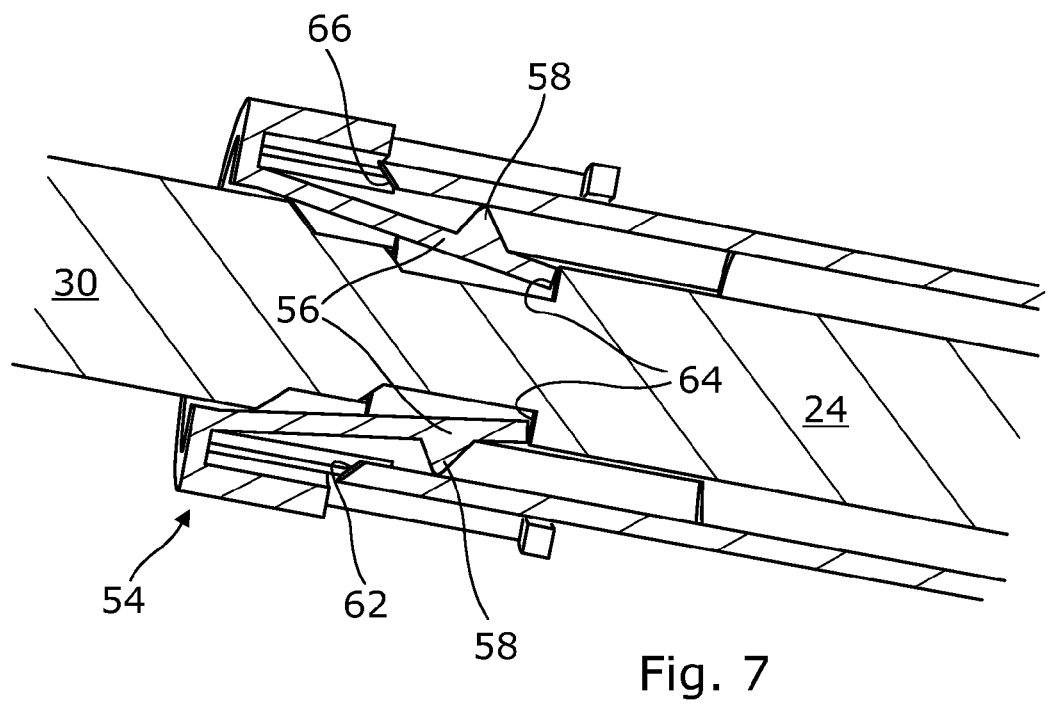
Figure 8:
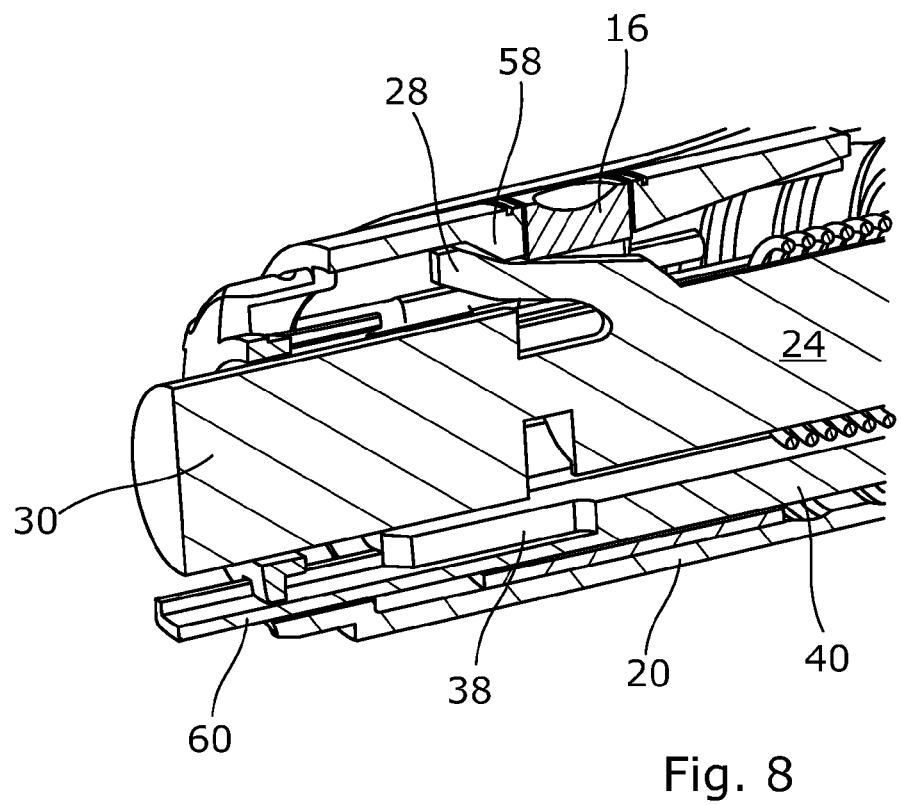
Figure 12A:
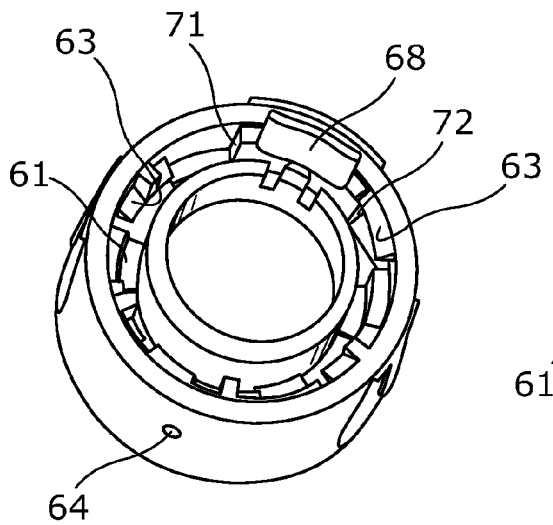
Figure 12B:
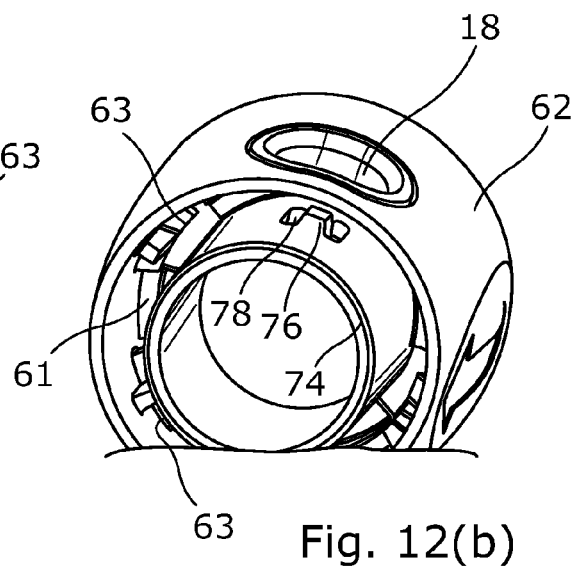
Figure 12C:
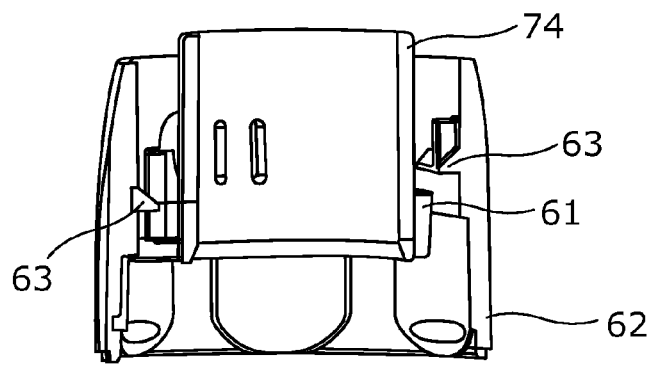
Figure 13:
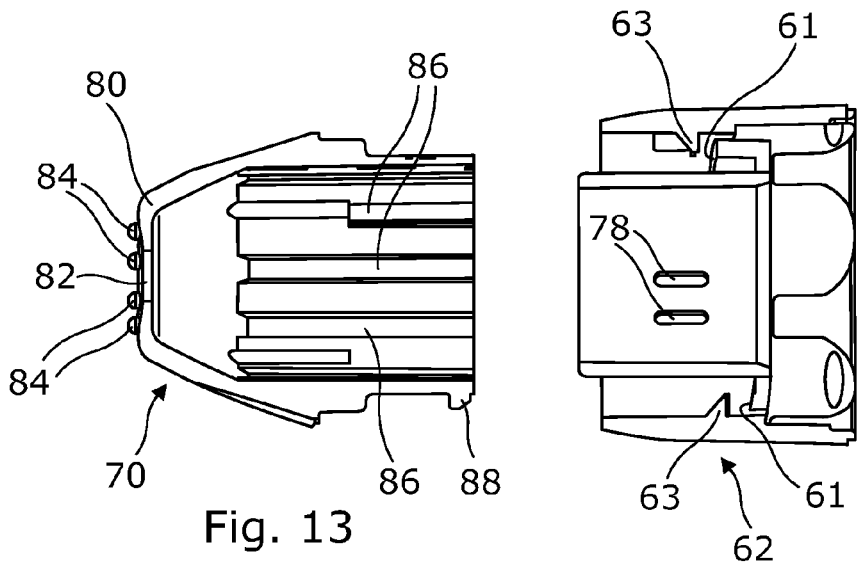

FIGS. 4(a) and 4(b) are detailed perspective view on a detail of the lancet release mechanism, with the blade element of the slider assembly removed for clarity;

FIG. 5 is a view of the slider assembly, lancet holder and trigger assembly for illustrating operating of the lancet holder lock;

FIG. 6 is a section view through the arrangement of FIG. 5 on an enlarged scale, prior to lock out of the lancet;

FIG. 7 is a view similar to FIG. 6 but showing the lancet holder in a lock out condition;

FIG. 8 is a detailed section view for the front end of the device, with the slider in a forward position;

FIG. 9 is a perspective view of the slider assembly, with the thumb pad removed, FIG. 10 is a view of the depth adjuster assembly when assembled;

FIG. 11 is an exploded view of the depth adjuster assembly;

FIGS. 12(a), 12(b) and 12(c) are enlarged views for illustrating the cam track profile on the rear portion on the depth adjuster assembly;

FIG. 13 is a cross section view through the front and rear portions of the depth adjuster assembly;

FIG. 14 is a perspective, part cutaway view of a second embodiment of this invention in which the slider assembly is biased by integrally formed spring portions, and FIGS. 15(a) and (b) are side views through a third embodiment of lancing device in accordance with the invention, in an armed state and a fired state respectively.

Figure 1:
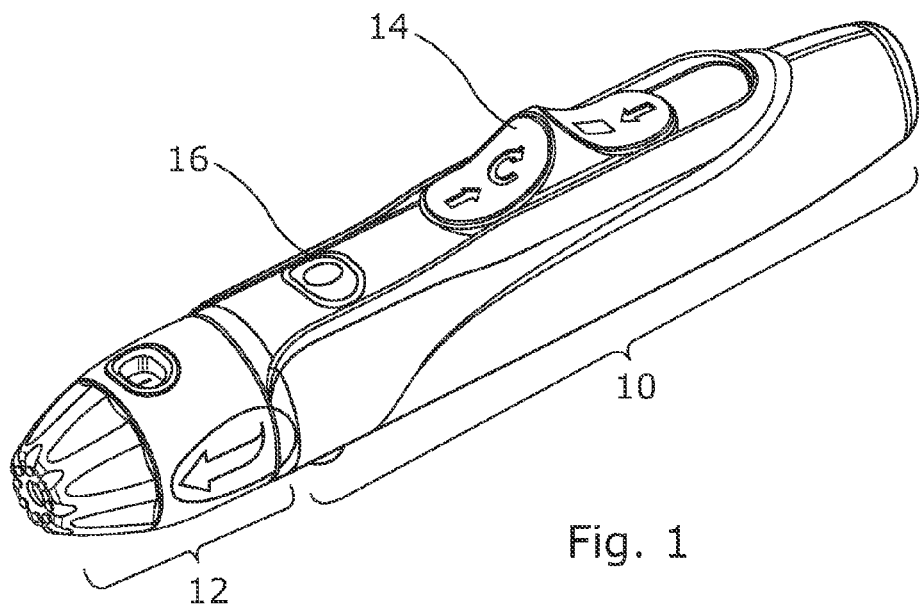
FIG. 1 is a general perspective view of an embodiment of lancing device in accordance with this invention.
Figure 2:
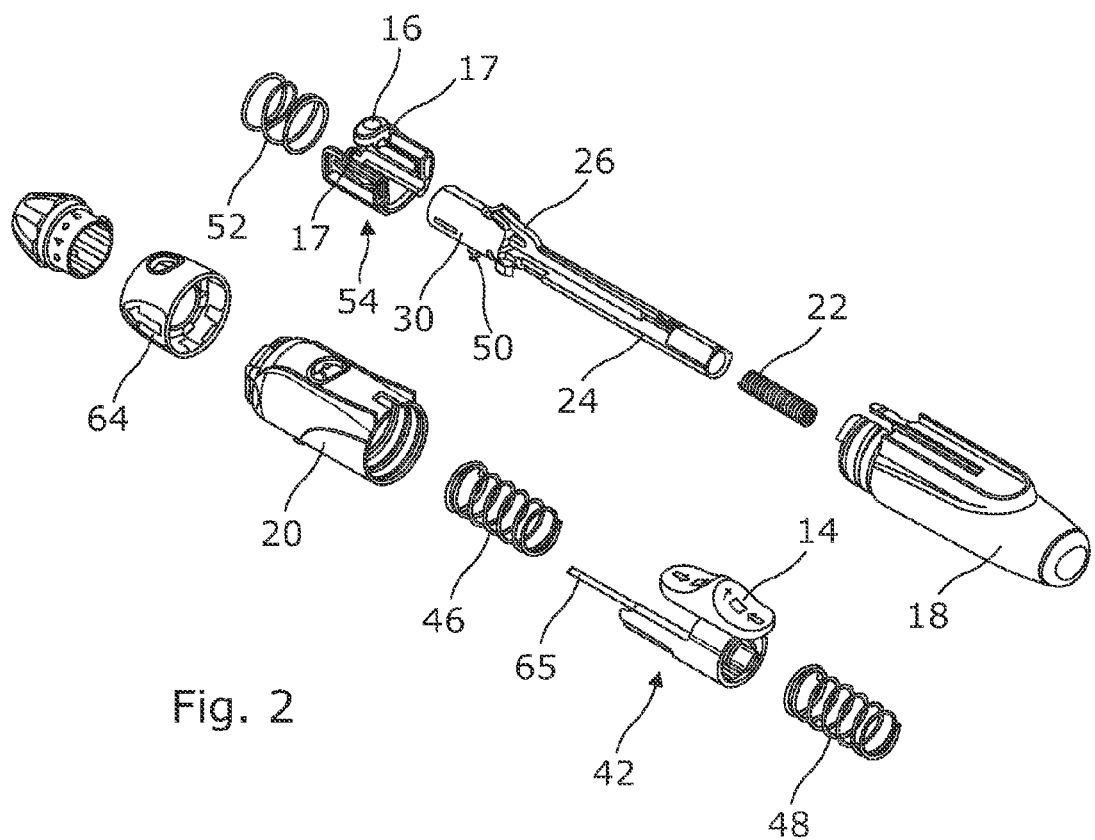
FIG. 2 is an exploded view of the device of FIG. 1.

Referring initially to FIGS. 1 and 2, the lancing device of this embodiment comprises a main housing 10 to the forward end of which is releasably attached a depth adjuster assembly 12. Projecting from the upper surface of the main housing 10 is an externally accessible thumb pad 14 of a slider assembly, the main part lying within the housing. The thumb pad 14 is slideable in the reverse direction (away from the depth adjuster assembly) to prime or cock the device prior to use, and further movable forwardly, after use, to release a spent lancet from the front of the housing when the depth adjuster assembly has been removed. The device is fired by pressing a firing button 16 which rises proud of the housing when the device is cocked.

As seen in FIG. 2, the main housing 10 is made up of a rear body portion 18 and a front body portion 20 which snap together. Disposed within and acting against a rear inner surface of the rear body portion 18 is a main drive spring 22, the forward end of which is received in a cylindrical recess in the rear part of a lancet holder 24. The lancet holder 24 is provided near its forward end with an integral resilient trigger latch finger 26 (visible on an in enlarged scale in FIGS. 3 and 8). When the lancet holder 24 is shifted back from the position shown in FIG. 3 by pressing rearwardly on the thumb pad 14, the trigger latch finger 26 snaps past an abutment 28 on the inner surface of the housing to latch behind it and, as it does so, pushes out the trigger button 16 so that it stands proud of the housing. At the front end of the lancet holder 24 is an integrally formed generally cylindrical socket 30 for receiving a lancet (not shown). As can be seen more clearly in FIGS. 4(a) and (b) an L-shaped slot extends down one side of the cylinder and circumferentially so as to provide staggered forward and rearward wall flaps that can be flexed or partially unwrapped to expand the effective internal diameter of the socket 30. Also as seen in FIGS. 4(a) and (b) two cammed abutments 34, 36 project radially from the external wall of the socket, one, 34, being disposed on the forward wall flap and the other, 36, disposed on the smaller, rearward wall flap. These abutments 34, 36 are offset with respect to each other, both angularly and longitudinally as shown. They cooperate with a guide slot 38 in a longitudinal projection 40 of a slider assembly 42 of which the thumb pad 14 is an integral part. The walls of the projection 40 defining the control slot 38 are also longitudinally staggered, and each include a chamfered gathering surface 44.

Figure 3:
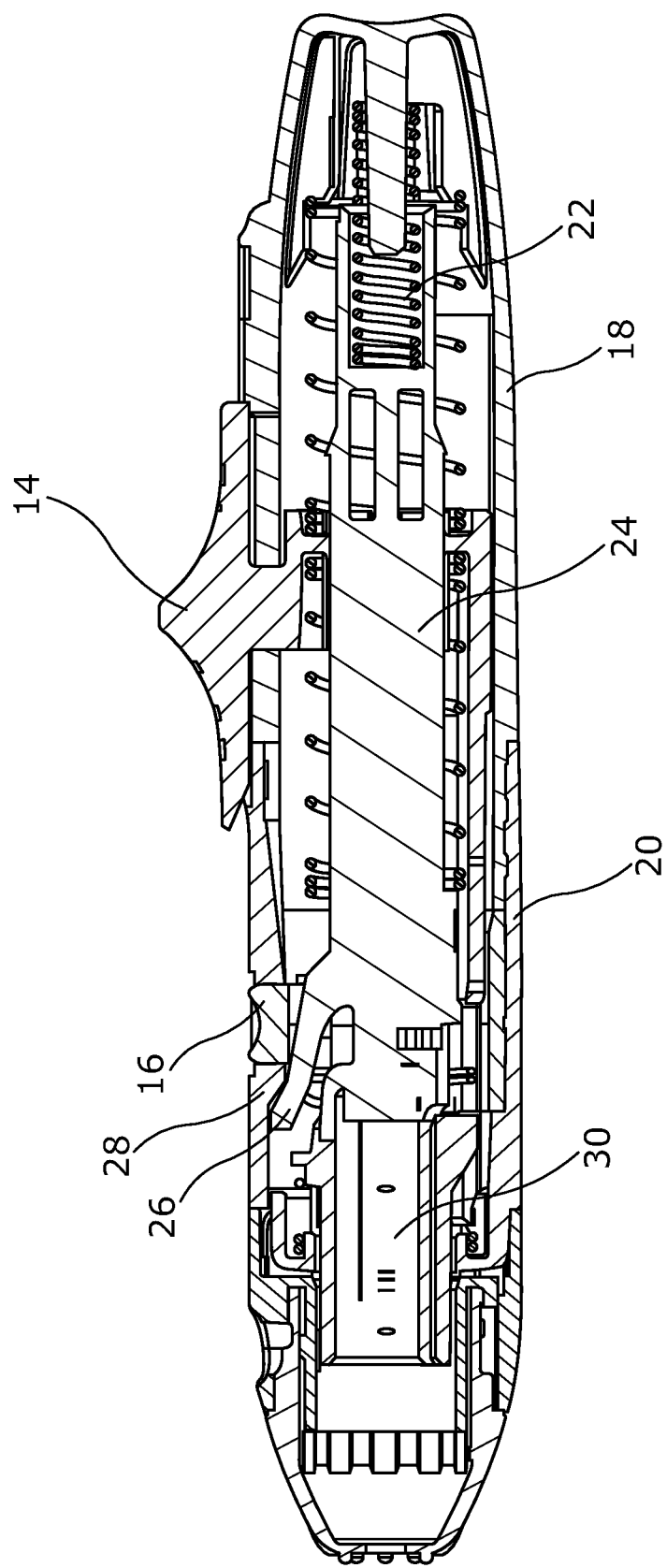
FIG. 3 is the longitudinal section view through the device of FIG. 1.

The slider assembly 42 is constrained for linear sliding movement forward and rearward from the position shown in FIGS. 1 and 3 against the influence of forward and a rearward bias spring 46, 48 respectively. Shifting the slider assembly forward engages the abutments 34 and 36 simultaneously to cause them to be urged into alignment to pass into the control slot 38. Doing this 'unwraps' the wall portions of the socket partially to expand it to allow a lancet to be loaded or unloaded with minimal insertion or withdrawal force respectively.

The socket 30 also has external projecting spring seats 50 which seat one end of a compression rebound spring 52, the other end of which is seated in an internal annular shoulder in the front body portion 20. Surrounding the forward end of the lancet holder 24 and located in the front body portion 20 against longitudinal movement is a trigger moulding 54 which resiliently carries the firing button 16 through two live hinges 17. As seen more clearly in FIGS. 5 to 7, the trigger moulding has two flexible lock out arms 56 on the outer surfaces of which are two ramp profiles 58. The lock out arms 56 are designed to cooperate with respective diametrically opposed slider arms 60, having chamfered leading edges 62. The slider arms 60 are an integral part of the slider assembly 42. The lancet holder 24 has a reduced width section behind the lancet receiving socket 30, defining two forward facing lock out shoulders 64. Sliding the slider assembly 42 forward from the position shown in FIG. 6 causes the slider arms 60 to engage the ramp profiles 58 on the lock out arms 56 to urge them inwardly to the position shown in FIG. 7, where they block forward movement of the lancet holder 24.

The slider assembly 42 includes in its base a prong or blade element 65 that projects forwardly one side of the projection 40, and which extends beyond the trigger moulding 54 to terminate just rearwardly of the front face of the front body portion 20, when the slider assembly 42 is in its rest position. The blade 65 is designed so that the slider assembly 42 cannot be moved forward from its rest position to release a lancet unless the depth adjuster assembly 12 has been removed.

Referring more particularly to FIGS. 10 to 13, the depth adjuster 12 is made up of a relatively fixed rear portion 66 that releasably connects to the front end of the front body portion by a snap fit or the like, in a single angular orientation, and which as noted blocks forward movement of the blade 65 when it is attached. Inside the rear portion 66 are interrupted, forward facing cam surfaces 61, 63 respectively, that define a helical cam track that functions as a thread. An aperture 68 in the rear portion allows indicia 69 on the front depth adjuster portion 70 to be viewed. Internally, the wall section adjacent said aperture is locally thickened to provide clockwise and anti-clockwise stops 71, 72 to restrict rotation of the front portion 70. The cam surfaces 61, 63 alternate and do not overlap in the axial sense and so this means that the rear portion 62 can be moulded which can be opened and closed axially without requiring a threaded mould piece that has to be threaded out of the mould. The rear portion 62 also includes an inner cylindrical sleeve 74 which generally surrounds the socket 30 of the lancet holder. On the outer cylindrical wall of the sleeve is a detent pip 76 with two slots 78 formed to allow resilient flexing of the detent pip.

The depth adjuster portion 70 comprises a frustoconical form element terminating in a transverse wall 80 with a lancet aperture 82 surrounded by equi-spaced projections 84, designed to provide a nerve distracting or confusion function. The remainder of the front depth adjuster part is internally splined 86 to cooperate with the detent pip 76 on the rear portion to provide a click or detent action as the depth adjuster is rotated. On the rear edge of the front portion 70 is formed a cam follower part 88 which is chamfered as seen in FIGS. 11 and 13, to allow it to snap past one or more of the cam surfaces 61, 63 on the rear portion 64. This means that the front and rear portions 66, 70 of the depth adjuster assembly 12 can be assembled simply by pushing one axially into the other, and no rotation is required. The snap action is designed to be sufficiently robust that the two parts cannot readily be separated once assembled. Once assembled, the front depth adjuster part can be rotated through approximately 270° with the rotation progressively adjusting the relative axial position thereby to vary the effective penetration depth of the lancing operation.

In operation of the device, having set the depth adjuster assembly 12 to give the required penetration, the depth adjuster assembly is removed from the front end of the device and the slider assembly 42 moved forward by thumb pressure on the thumb pad 14 to release a spent lancet (if present) by expanding the socket 30 of the lancet holder due to the action of the abutments 34, 36 being gathered into the slot 38 of the projections 40. Whilst held in the expanded position, a fresh lancet may be located in the lancet holder without requiring any significant axial force. Having inserted the lancet, the slider is allowed to return to its rest position and returning the socket to its non-expanded form, thereby gripping the lancet. The depth adjuster assembly 12 is then re-applied to the front of the device and the device cocked by sliding the slider rearwardly. The slider assembly engages the lancet holder and pushes it back against the force of the drive spring 22 until the resilient finger 26 snaps rearwardly past the abutment 28 on the housing to latch and in so doing, pushes the trigger button 16 proud. The user will then offer the device up to the penetration site and fire the lancet by pressing button 16.

In a modification, not shown, the thumb pad 14 may be extended forwardly so that, in its rest position, its forward edge lies just to the rear of the aperture in which the trigger button 16 sits. By doing this, when the device is cocked and the trigger button 16 pushed proud of the housing by latching of the lancet holder, the lancet button blocks forward movement of the thumb pad 14 and so it is not possible to move the slider forward until after the device has been fired.

In a second embodiment, shown in FIG. 14, the forward and rearward bias springs 46 and 48 that bias the slider assembly may be replaced by integrally moulded spring portions $46^1$, $48^1$, thereby further reducing the component count.

Referring now to the third embodiment, this is similar in construction to the previous embodiments and like components are given the same reference numerals and will not be described in detail again. In the first and second embodiments, when the device is fired, forward travel of the lancet holder 24 is limited by a forward facing abutment surface on the lancet holder moving into abutment with a rearward facing abutment surface on the housing or a component associated therewith. In the third embodiment, forward travel of the lancet holder 24 is limited by a forward facing abutment surface 90 on a formation 92 at the rear end of the lancet holder 24 engaging a rearward facing shoulder 94 protruding inwardly from the housing wall.

The invention claimed is:

1. A lancing device having:
    a housing comprising
        a main body portion, and
        a forward nose portion that is removably attached to the main body portion to allow loading and unloading of a lancet in use;
    a lancet holder movably mounted in said housing and having a forward portion for receiving a lancet in use; and
    a lancet release element movable among
        an intermediate rest position,
        a rearward position in which the lancet release element cocks the lancing device in a ready-to-fire position prior to use, and
        a forward release position to release the lancet from the lancet holder,
    said lancet release element comprising an elongate extension that is exterior to an outer periphery of said lancet holder, wherein forward movement of the elongate extension is prevented by said forward nose portion when said forward nose portion is connected to said main body portion so that forward movement of said lancet release element from the intermediate rest position to the forward release position is prevented by said forward nose portion when the nose portion is connected to said main body, and
    wherein said lancet release element is movable from the intermediate rest position to said forward release position only after said forward nose portion is removed from said main body portion, and
    wherein said lancet release element is movable longitudinally and wherein a forward end of said elongate extension directly contacts said forward nose portion to prevent the forward movement of said lancet release element when the forward nose portion is connected to said main body portion.

2. The lancing device according to claim 1, further comprising the lancet, wherein said lancet comprises a movable insertion element disposed in said housing and having a sharp tip and adapted to be inserted into skin of a recipient; and
    wherein said forward nose portion comprises a depth penetration arrangement comprising, a first, relatively fixed portion forming part of or secured to said housing, and a skin contacting portion being mounted for angular movement about an axis on said relatively fixed portion;

wherein one of the relatively fixed portion and the skin contacting portion has an interrupted cam surface, and the other of said relatively fixed portion and said skin contacting portion has a cam follower adapted to cooperate with said interrupted cam surface, whereby rotation of said skin contacting portion relative to said fixed portion varies the relative axial position of said skin contacting portion and said fixed portion.

3. The skin penetration device according to claim 2, wherein said relatively fixed portion and said skin contacting portion include respective detent elements to prevent a detent action at spaced angular positions.

4. The skin penetration device according to claim 2, wherein a stop surface is associated with said interrupted cam surface to limit rotation of said skin contacting portion relative to said fixed portion.

5. The skin penetration device according to claim 2, wherein said interrupted cam surface follows a generally helical path with respect to the axis, the cam surface including alternate opposite facing cam face elements together defining a cam track for said cam follower.

6. The skin penetration device according to claim 5, wherein the cam face elements are of lesser circumferential extent than said cam follower.

7. The skin penetration device according to claim 5, wherein at least one of the cam surface and said cam follower are resiliently deformable to allow said cam follower to be introduced into said cam track by application of an axial load.

8. The skin penetration device according to claim 5, wherein said cam follower is provided on said skin contacting portion and said cam track is provided on said relatively fixed portion.

9. The lancing device according to claim 1, wherein said lancet release element is movable in a direction generally parallel to a lancing direction.

10. The lancing device according to claim 1, wherein the elongate extension projects forwardly to terminate just rearwardly of a front face of the main body when the lancet release element is in the intermediate rest position.

* * * * *